United States Patent
Lajoie-Dorval (10) Patent No.: US 9,089,387 B2
(45) Date of Patent: Jul. 28, 2015

(54) SURFACE MANIPULATION IN DENTAL PROSTHESIS DESIGN

(75) Inventor: Jean-Philippe Lajoie-Dorval, Quebec (CA)

(73) Assignee: BIOCAD MEDICAL, INC., Nord Quebec (CA)

( * ) Notice: Subject to any disclaimer, the term of this patent is extended or adjusted under 35 U.S.C. 154(b) by 800 days.

(21) Appl. No.: 12/842,108

(22) Filed: Jul. 23, 2010

(65) Prior Publication Data

US 2012/0022834 A1  Jan. 26, 2012

(51) Int. Cl.
G06F 17/50 (2006.01)
A61C 13/00 (2006.01)
G06F 19/00 (2011.01)

(52) U.S. Cl.
CPC ........ *A61C 13/0004* (2013.01); *G06F 19/3437* (2013.01)

(58) Field of Classification Search
None
See application file for complete search history.

(56) References Cited

U.S. PATENT DOCUMENTS

| 2006/0020363 A1* | 1/2006 | Orth et al. ............... 700/187 |
| 2006/0115793 A1* | 6/2006 | Kopelman et al. ......... 433/215 |
| 2011/0196654 A1 | 8/2011 | Genest et al. |

FOREIGN PATENT DOCUMENTS

WO   WO 2007/084727   7/2007

OTHER PUBLICATIONS

Jan. 23, 2013 International Preliminary Report, Written Opinion and International Search Report for International Application No. PCT/EP2011/003379 filed on Jul. 7, 2011.

* cited by examiner

*Primary Examiner* — Omar Fernandez Rivas
*Assistant Examiner* — Cuong Luu
(74) *Attorney, Agent, or Firm* — Knobbe, Martens, Olson & Bear LLP (57) ABSTRACT

Herein are provided methods, systems, computer-readable media, techniques and processes for surface manipulation in dental prosthesis design. These include providing an interface for modifying the surface of a model of a dental prosthesis. This interface may be provided to an operator, dentist, dental practitioner, or any other appropriate person via a computer and a computer display. The operator provides areas in which the operator would like to add a layer or other limited manipulation to the surface of the model. This may include an addition to the surface or a subtraction from the surface. As the operator is defining additional areas to manipulate on the surface (e.g., add or subtract a layer), invariably some of them will overlap. Unlike previous methods, this overlap will not cause the amount added to the surface to increase beyond the predefined limit for the layer. This allows operators to define cleanly added layers or cleanly subtracted layers from dental prostheses.

18 Claims, 12 Drawing Sheets

SURFACE MANIPULATION IN DENTAL PROSTHESIS DESIGN

BACKGROUND

1. Field

The present application generally relates to dental planning, and more particularly to surface manipulation in dental prosthesis design.

2. Description of Related Technology

The use of computer systems to design dental prostheses has increased in recent years. The computer systems allow a dentist, dental technician, or other operator to design dental prostheses for individual patients. These individual prosthesis designs are often called "situations," "dental plans," or "prosthetic plans." Operators using the computer systems can design plans based on a library of the teeth shapes and positions, patient data, and available equipment and hardware.

A problem with current systems is that they provide only limited ways to manipulate the surface of the dental prostheses that are being designed. These limited manipulations can make it difficult for an operator to add or subtract relatively uniform "layers" of material to/from the surface of a dental prosthesis that is being designed. Adding and subtracting uniform layers of material can be important when operators would like to thicken a portion of a crown or prosthesis for stability reasons and increase the thickness of a crown without significantly altering the contour, just to name a few examples. These problems and others are addressed by the techniques, systems, methods, devices, and computer-readable media described herein.

SUMMARY

Presented herein are methods, systems, devices, and computer-readable media for surface manipulation in dental prosthesis design. This summary in no way limits the invention herein, but instead is provided to summarize a few of the embodiments.

Embodiments herein include systems and methods for surface manipulation in dental prosthesis design. For example, embodiments include providing a computer-based interface for modifying a surface of a model of a dental prosthesis; receiving via the computer-based interface a set of areas where an operator would like to perform a limited manipulation of the surface of the model; and manipulating portions of the surface up to a limit associated with the limited manipulation of the surface based on the set of areas, irrespective of overlap in the areas received from the operator. Embodiments may also include receiving a first area in the set of areas and a second area in the set of areas, wherein the first area and the second area overlap in a particular, overlapping area; and manipulating portions of the surface associated with the particular, overlapping area only up to the limit associated with the limited manipulation, notwithstanding the overlap.

Numerous other embodiments are described throughout herein.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

DETAILED DESCRIPTION OF SPECIFIC EMBODIMENTS

Overview

Traditionally, when designing dental prostheses, operators, dentists, and dental practitioners manipulate the surfaces of the model of the dental prostheses they are designing. Manipulation options may be limited. For example, a system might allow an operator to select among a limited number of points on the surface, and to pull, push, or move those points in order to modify the surface itself. Even in hypothetical systems where the operator can manipulate more than a limited number of points, this type of manipulation would be awkward or cumbersome.

Another option might be to allow the operator to "spray" material onto the surface of the prosthesis. In doing so, the surface of the prosthesis would be modified based on the rate of spray and the amount of time of spray. Therefore, if an operator wanted to add a significant amount of material at one point, the operator can hold the spray at that one point, and the surface will continue to deform in the opposite direction of spray.

In any of these approaches for designing dental prostheses, it would be very difficult to add or cut away a layer to/from a dental prosthesis. Various methods, systems, techniques and computer-readable media described herein enable the operator to add relatively uniform layers to the surface of a prosthesis or to subtract relatively uniform layers from the surface of a prosthesis.

Figure 1:
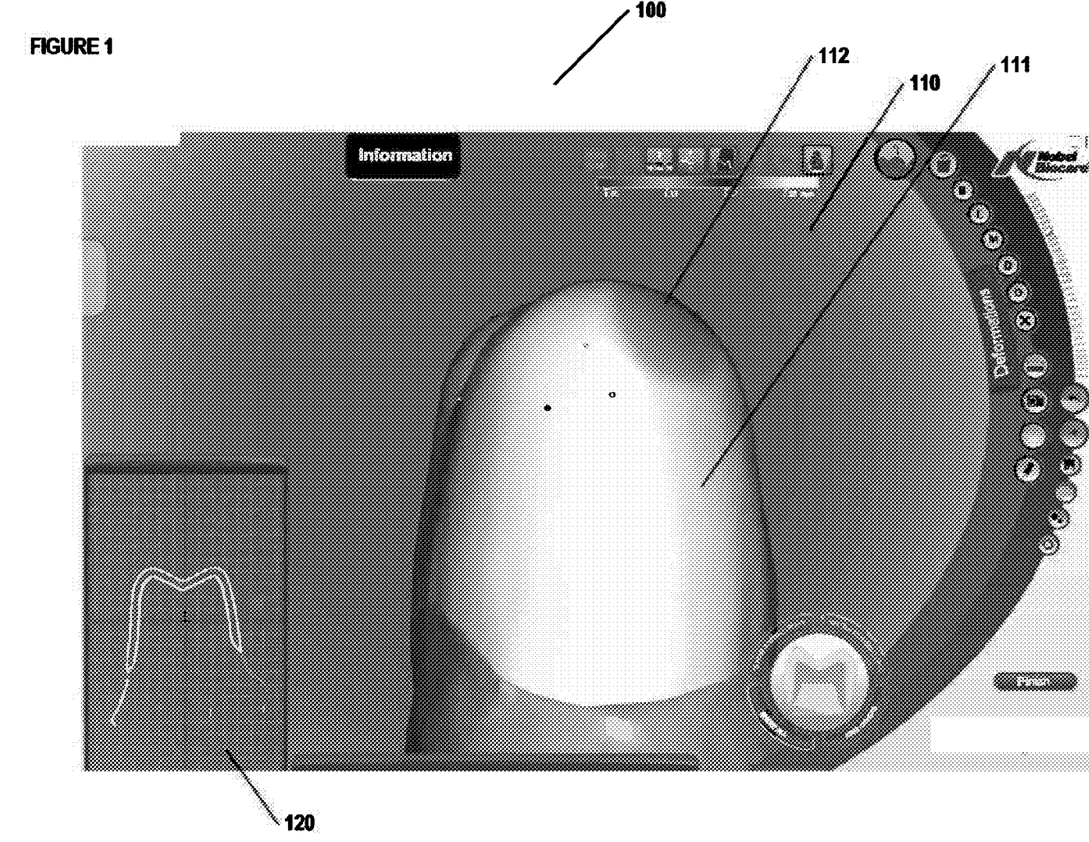
FIG. 1 illustrates a first interface for surface manipulation in dental prosthesis design.

FIG. 1 shows an example of an interface 100 that includes an overlaid representation portion 110, as well as a cross-section portion 120. The overlaid representation portion 110 shows the surface of a model 111, that surface being a representation of the dental prosthesis being designed. Various embodiments described herein will allow an operator to manipulate a mouse, either 2D or 3D, a keyboard, or other input device, in order to add or subtract a uniform layer to the surface 111 of the dental prosthesis. The view of the surface as the model is being manipulated may be marked or colored 112 to show the position of where the mouse is manipulating or will manipulate the surface 111.

In some embodiments, the user uses the input device in order to define a set of areas in which the uniform layer is to be added. These sets of areas can overlap without changing the uniformity of the layer being added or subtracted. This is in sharp contrast to the spray paint method in which any overlap will cause additional deposit of material on the surface. In various embodiments, the operator can indicate the start of a layer deposition using a mouse click, keystroke or other input, and begin to manipulate the mouse in order to define a line, set of points, set of areas, or other indication of where the layer should go. The areas defined by this input will be manipulated (e.g., a layer added or subtracted) up to a limit associated with the layer, regardless of the overlap among the areas.

An operator may want to add a uniform layer to the surface of a prosthesis in order to provide additional girth or width to the prosthesis without changing the general anatomic shape of the area being manipulated. Another reason that an operator may want to add a uniform layer is to provide a veneer on or thicken a cut-back restoration. The other previous manipulation methods will not necessarily provide as easy an interface for adding such a uniform layer.

The types of manipulation described herein may be used with full anatomic restorations, full contour restorations, and/or cut-back restorations. The model used as input to the system can be a scan of a dental wax up, can be a CAD model of a dental plan built up in a CAD design program, or can come from another source. Further, these manipulations may be used with any type of dental prosthesis design.

Additional embodiments and further description are provided below.

Example System

Figure 2:
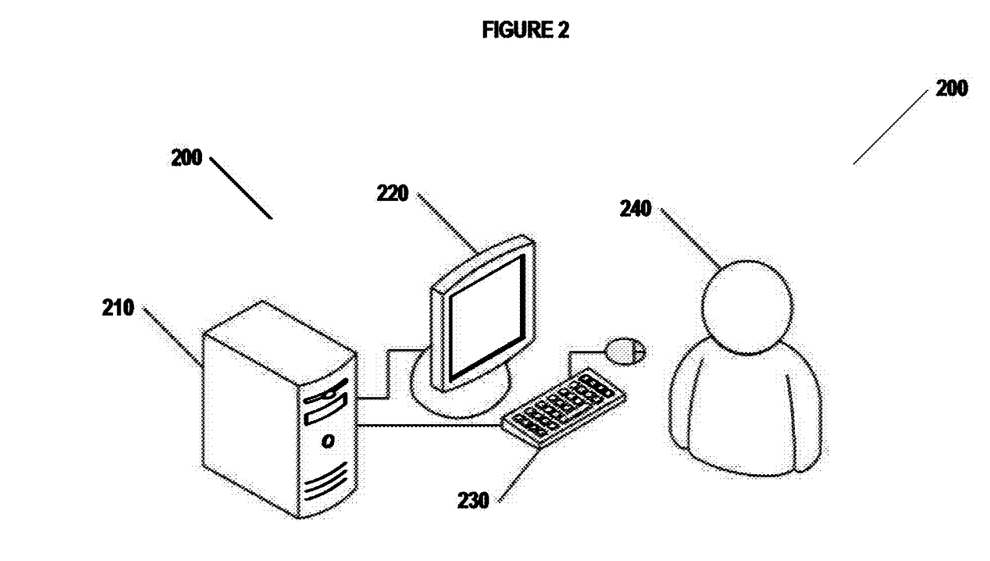
FIG. 2 illustrates an example system for surface manipulation in dental prosthesis design.

FIG. 2 illustrates an example system 200 for surface manipulation in dental prosthesis design. The system 200 may include one or more computers 210 coupled to one or more displays 220, and one or more input devices 230. An operator 240, who may be a dentist, dental technician, or other person, may plan dental prostheses using system 200 by manipulating the one or more input devices 230, such as a keyboard and/or a mouse. In some embodiments, while working on the dental plan, the operator 240 may view the dental plan and other related dental plan data on the display 220. The display 220 may include two or more display regions or portions, each of which displays a different view of the dental plan. For example, in some embodiments, the display 220 may show a semi-realistic 3D rendering of the dental plan, a localized abstraction of the dental plan, and/or a cross-sectional representation of the dental plan. Each of these displays or portions may be linked internally within a program and/or using data on computer 210. For example, a program running on a computer 210 may have a single internal representation of the dental plan in memory and the internal representation may be displayed in two or more abstract or semi-realistic manners on display 220.

In some embodiments, the operator 240 may be able to perform a command, such as select, move, manipulate, or make transparent, opaque, or invisible, on a particular sub-structure in the dental plan. The operator 240 may be able to perform this command by manipulating the input device 230, such as clicking with a mouse on a particular region of one of the abstract or semi-realistic versions of the dental plan displayed on the display 220.

In various embodiments, the computer 210 may include one or more processors, one or more memories, and one or more communication mechanisms. In some embodiments, more than one computer may be used to execute the modules, methods, blocks, and processes discussed herein. Additionally, the modules and processes herein may each run on one or multiple processors, on one or more computers; or the modules herein may run on dedicated hardware. The input devices 230 may include one or more keyboards (one-handed or two-handed), mice, touch screens, voice commands and associated hardware, gesture recognition, or any other means of providing communication between the operator 240 and the computer 210. The display 220 may be a two-dimensional ("2D") or 3D display and may be based on any technology, such as LCD, CRT, plasma, projection, etc.

The communication among the various components of system 200 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 200 may also be combined into a single unit or module. In some embodiments, all of the electronic components of system 200 are included in a single physical unit or module.

Process for Surface Manipulation in Dental Prosthesis Design

Figure 3A:
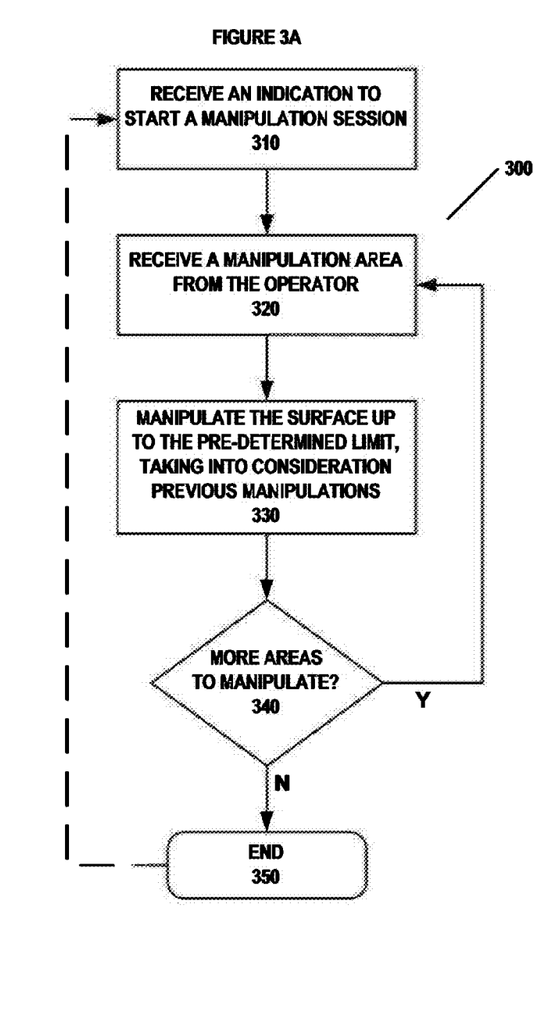
FIGS. 3A and 3B illustrate two example methods for surface manipulation in dental prosthesis design.
Figure 3B:
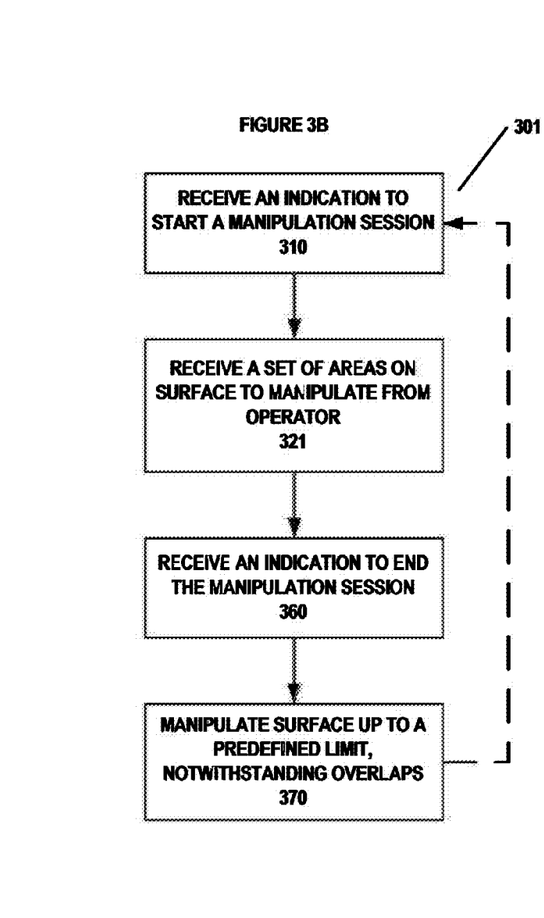

FIGS. 3A and 3B depict methods for surface manipulation in dental prosthesis design. In an example embodiment, an operator desiring to add a uniform layer to the model for a crown may move the cursor with the mouse over the crown, press the mouse button, and start moving the mouse around in order to define on what parts of the crown should have the uniform layer added. When the operator releases the mouse button, the addition of that uniform layer ends. No area on the crown has more than the predefined limit of layer added, regardless of how many times the operator may have dragged the cursor over the any particular area. In various embodiments, the edges of the area defined by the operator (the 'border band') may be tapered. Additionally, in some embodiments, an operator can similarly remove or 'slice off' a uniform layer. In some embodiments, the operator can see the uniform layer as it is being added (during the mouse movements). In other embodiments, the operator sees the addition of the uniform layer after the session has ended. Various other techniques, embodiments, and methods are described further herein.

Returning to FIG. 3A, in block 310, an indication is received to start a manipulation session. The indication may be a mouse click, a keystroke, a gesture with a 3D mouse, a verbal signal, or any other type of input. The operator, by indicating the start of a manipulation session, is indicating that the subsequent areas defined during the manipulation session will all be part of the same manipulation. The indication to start a manipulation session may signal, for example, the addition of a layer to the surface or the subtraction of a layer from the surface. For example, a left mouse click might indicate an addition to the surface, and a right mouse click might indicate the subtraction from a surface. Keystrokes may also be used to signal the addition or subtraction of a layer. For example, control-X might indicate a manipulation session that will subtract from the surface, and a control-V might indicate the start of a session to add a layer to the surface. As another example, a manipulation session may start when the left mouse button is first held down, and the manipulation session may continue until the left mouse button is released.

After an indication to start a manipulation session is received in block 310, then in block 320, a manipulation area is received from the operator. One way in which an operator can specify a manipulation area is by dragging a mouse cursor over the surface in an overlaid representation portion, such as overlaid representation portion 410 in FIG. 4. The manipulation area specified by the operator in that case may be a single location with an associated radius or area that is to be manipulated. In some embodiments, the operator, may move the mouse over a surface, and then click a mouse button or press a keyboard key, in order to indicate an area to be manipulated. Block 320 may be performed numerous times to receive a set of manipulation areas, as depicted in FIG. 3A.

Herein described are various 'areas' on a surface. The area on the surface may be defined by a location and a radius, that location being a point on the surface of the model. The multiple or sets of areas may be defined by a line from one point on the model to another point on the model, or a curve from one point on the model to another point on the model. In some embodiments, the area may not be circular, but may be an object with a spine that's associated with the line or the curve defined on the surface. In some embodiments, if the operator decides to remove the layer that has been added, the operator may hit a keystroke, provide a verbal signal that will 'undo' the last action.

After a manipulation area has been received from the operator in block 320, then in block 330, the surface is manipulated up to the predetermined limit, taking into consideration previous manipulations performed during this manipulation session. Therefore, if the area received in block 320 has already been manipulated up to the predetermined limit during this manipulation session, then the surface will not be manipulated any further. If a portion of the surface received from the operator in block 320 has already been manipulated, then the remaining portion of the surface may be manipulated up to the predetermined limit in block 330. As such, consider an operator that is indicating areas to be manipulated by dragging a mouse across the surface by, for example, while holding down a mouse button. Due to the cohesive nature of the path that the mouse will be dragged, the areas to be manipulated that are received in block 320 may overlap, either partially or substantially, and therefore, each subsequent manipulated area may cause only a small portion of the surface to be manipulated (because much of any current area will have been manipulated in previous iterations of block 330).

Figure 8:
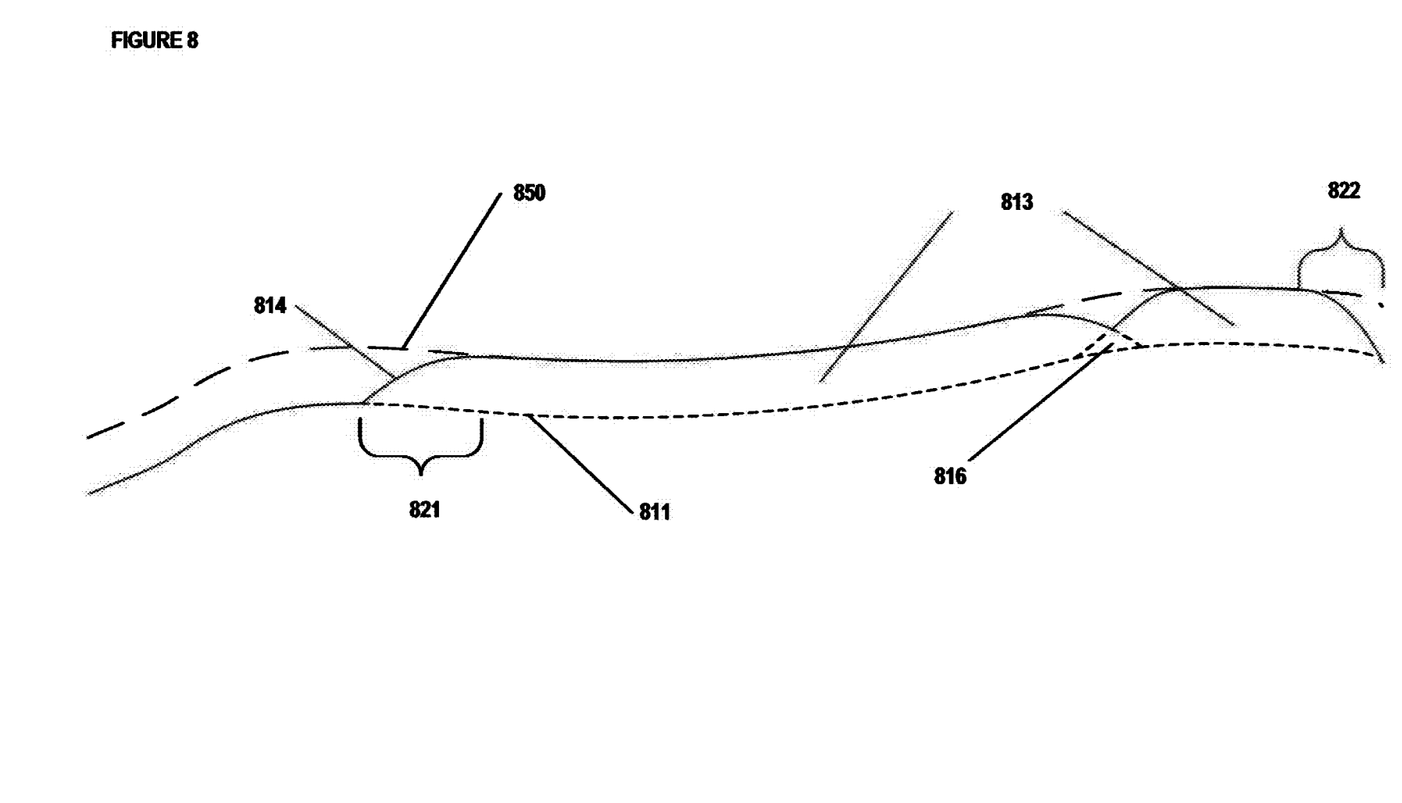
FIG. 8 illustrates a first surface manipulation in dental prosthesis design.

In some embodiments, the area to be manipulated may have a tapered edge. This is depicted in FIG. 8. The area to be manipulated, 813, may have a tapered edge 814. Therefore, part of the area to be manipulated, 813, will be manipulated up to the manipulation limit 850 above the original surface 811. As depicted in FIG. 8, the tapered edge 814 may go from the manipulation limit 850 down to the original surface 811.

In certain embodiments, if there is an overlap of the tapered edge, such as depicted by overlapped tapered edge 816, then the amount that the original surface 811 is manipulated may be a function of the amount that each of the tapered edges would have manipulated the surface at that point. This function may be additive, thereby adding to the surface, up to the manipulation limit 850, based on the overlap depicted at 816. In some embodiments, the amount to manipulate the surface at an overlapped tapered edge 816 may be the maximum that either of the tapered edges would have individually manipulated the surface. Therefore, in some embodiments, if at a particular point along the surface 811, one tapered edge would have manipulated the surface by 80% of the manipulation 850, and the other would have manipulated the surface by 70% of the manipulation limit 850, then the amount that the surface will be manipulated would remain 80% of the manipulation limit 850.

The tapered edges of an area to be manipulated may be defined by a 'border band,' depicted in FIG. 8 as 821 and 822. The border band 821 and 822 may be a small area encircling the area to be manipulated, or it may be a band at the edge of the area to be manipulated. The amount that the surface is manipulated over that border band 821 and 822 may be tapered, as a straight line, as a curve (as depicted in FIG. 8), as a sinusoid, or in any appropriate manner. Points beyond the border band may be manipulated by zero, or in other words, may not be manipulated at all, and the surface would remain at the same level.

Returning again to FIG. 3A, the determination, in block 340, whether there are more areas to manipulate may include receiving a mouse click, mouse gesture, 3D mouse gesture, keyboard stroke, etc., or any other signal indicating that the manipulation session should end. If that signal has not been received, then the process may return to block 320 to receive another manipulation area from the operator. If there are no more areas to manipulate, as determined in block 340, then in block 350, the manipulation session is terminated. Optionally, the process may include waiting for or otherwise receiving another indication to start another new manipulation session in block 310, and the process 300 may begin over again.

The blocks in process 300 may be performed in any order, and additional blocks may be added. Further, certain blocks may be consolidated or omitted altogether. For example, in FIG. 3B, a process 301 for surface manipulation in dental prosthesis design is shown. As was the case in process 300, process 301 begins by receiving an indication to start a manipulation session. After that indication is received, a set of areas on the surface to manipulate are received. This set of areas may be received from an operator, and may be received in any of the manners described with respect to process 300, including an operator dragging a mouse to indicate areas, or any other manner. The manipulations associated with these received areas to manipulate may be displayed to the operator immediately, or may be displayed after a certain period of time, or may be displayed after the manipulation session has ended.

The sets of areas to be manipulated are received in block 321 until an indication to end the manipulation session has been received in block 360. This indication to end the manipulation session may take any of the forms described with respect to process 300. In block 370, the surface is manipulated up to a predefined limit, notwithstanding any overlaps. The amount to which to manipulate the surface may be determined by looking at all of the areas for which manipulation is desired, and for those areas, manipulating the surface up to the predefined limit. In this way, the process can wait until an entire session's worth of areas are received from the operator before determining the overlap and the surface manipulation.

As another example, in some embodiments, a manipulation session may be started by pressing a key stroke (e.g., block 310), then areas to manipulate may be indicated by successive clicks of a mouse button (e.g., block 320 or 321), and another keystroke may signal the end of the manipulation session (e.g., block 340 or 360). In some embodiments, the start of a manipulation session may be signaled by a left mouse click (e.g., block 310) and the areas to manipulate may be selected with a right mouse click (e.g., block 320 or 321)—and a subsequent left mouse click may signal the end of the manipulation session (e.g., block 340 or 360).

Examples Interfaces for Surface Manipulation in Dental Prosthesis Design

Figure 4:
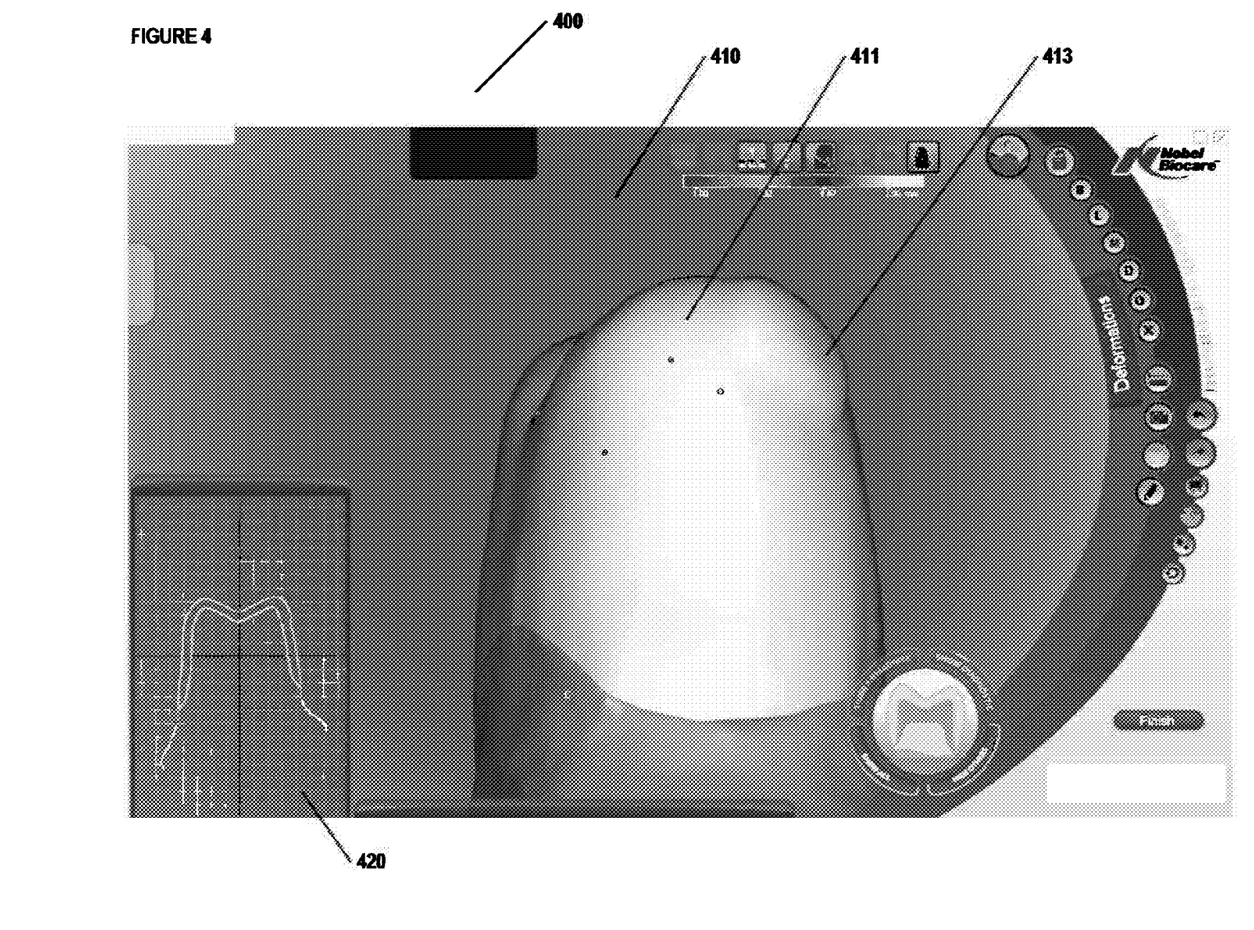
FIG. 4 illustrates a second interface for surface manipulation in dental prosthesis design.

FIG. 4 shows an interface 400 that includes an overlay representation portion 410 and a cross-section portion 420. The overlay representation portion 410 shows the surface 411, as well as a previously manipulated portion of the surface 413.

Figure 5:
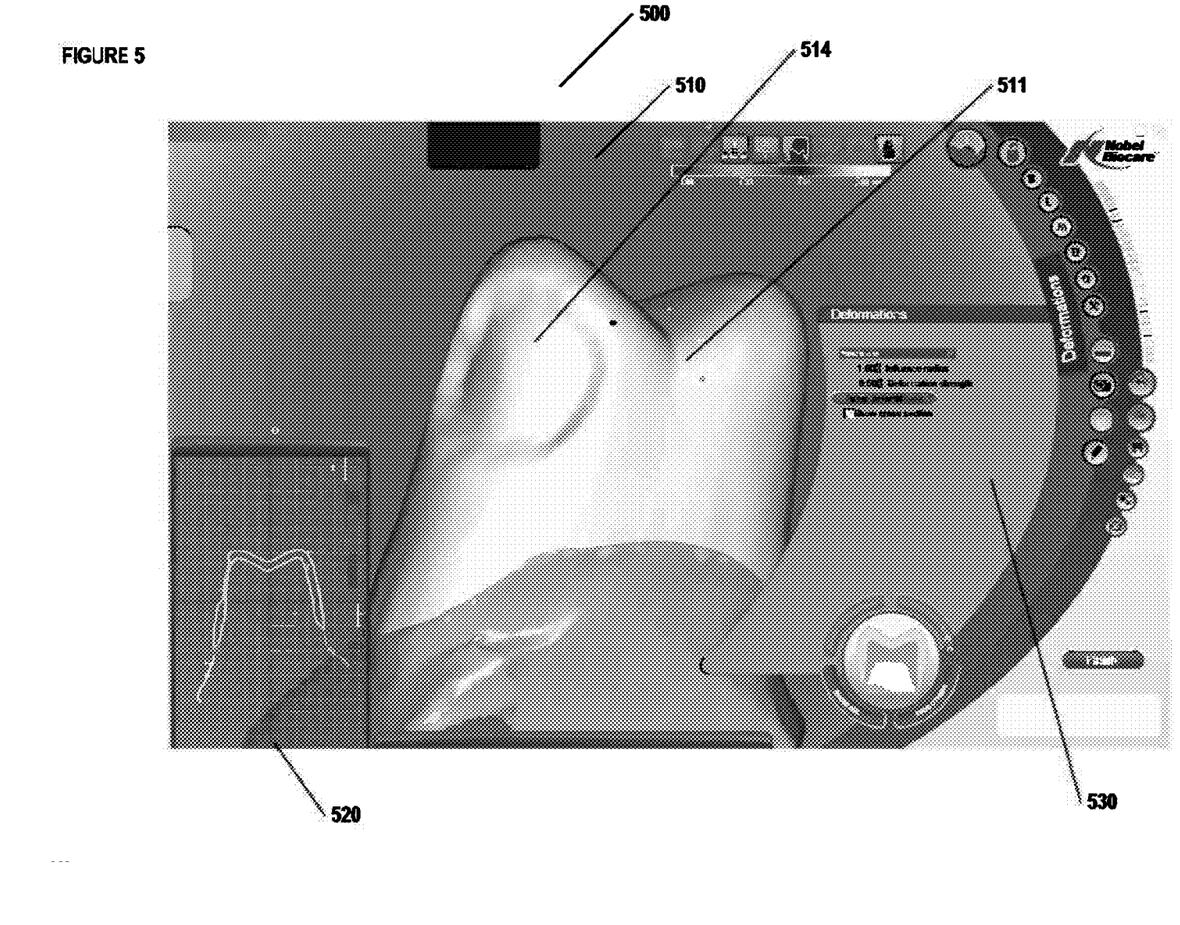
FIG. 5 illustrates a third interface for surface manipulation in dental prosthesis design.

FIG. 5 shows another interface 500 for surface manipulation in dental prosthesis design. The interface 500 includes an overlaid representation portion 510, a cross-section portion 520, and a manipulation menu 530. In some embodiments, the manipulation menu 530 may be visible at all times to the operator. In other embodiments, the manipulation menu may be hidden or partially hidden on the interface 500, and may be pulled out, clicked on or otherwise opened, for example, with a keystroke, before it is shown. For example, the manipulation menu 530 may be opened as a drop-down box or by performing a shortcut key. The manipulation menu may include a counter, textbox, or other manner of changing the manipulation limit associated with subsequent layers. That is, the manipulation menu 530 may allow the operator to change the thickness of a layer (e.g., the 'deformation strength' of the manipulation) to be added or subtracted from the surface 511. The thickness of the manipulation layer to be added or subtracted from the surface 511 may be changed in numerous ways, including holding down a keyboard key, such as the control key, and manipulating the mouse or the mouse wheel. The manipulation menu may also have a radius or area of influence portion that will allow the operator to define how wide the areas to be manipulated should be defined. The radius (e.g., the 'influence radius') of the manipulation areas for the surface 511 may also be changed in myriad ways, including holding down a keyboard key, such as the shift key, and manipulating the mouse or the mouse wheel.

Figure 6:
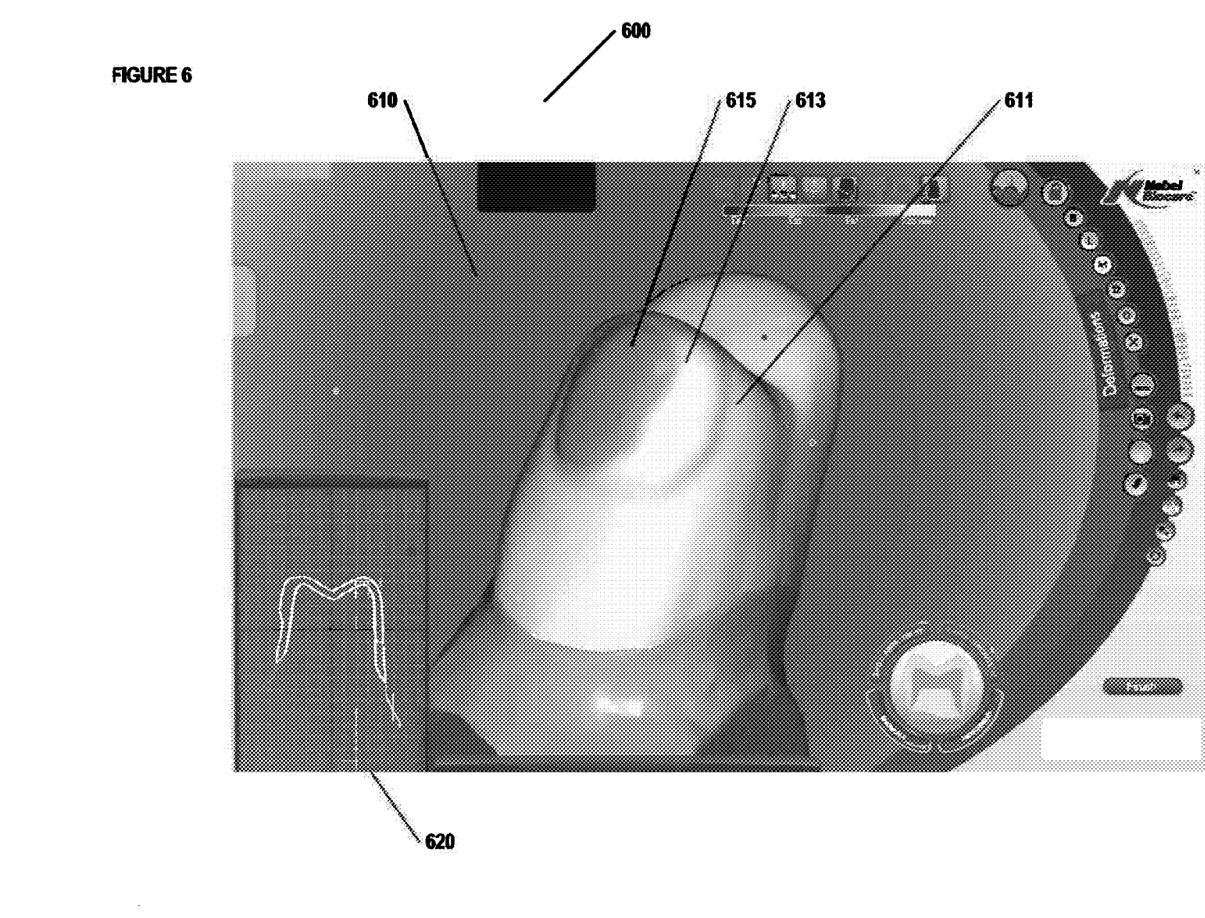
FIG. 6 illustrates a fourth interface for surface manipulation in dental prosthesis design.

FIG. 6 shows another example of an interface for surface manipulation in dental prosthesis design. Interface 600 includes an overlaid representation portion 610 and a cross-section portion 620. The surface 611 is shown in the overlaid representation portion 610. On the surface 611 is a previously manipulated portion of the surface 613 and visible in darker color is a currently manipulated portion of the surface 615. The previously manipulated portion of the surface 613 is associated with its own (now-closed) manipulation session. Subsequent to that manipulation session, the layer added during that manipulation session is considered part of the underlying surface (e.g., surface 611). Therefore, when the next manipulation session starts, the second manipulation portion 615 may be added on top of the previously manipulated portion, thereby adding two layers to what had been the underlying surface 611.

Turning to the cross-section portion 620, the cross-section portion may show the cross-section of the surface, as well as underlying structures, such as coping or supporting teeth. The cross-section portion may allow an operator to look at the thickness of a crown or other structure being added to the dental prosthesis design. Certain dental prosthesis designs require thicknesses based on material, required strength, or other parameters. The cross-section portion may allow the operator to quickly view the thickness and therefore know to what portions of the surface 611 to add layers.

Figure 7:
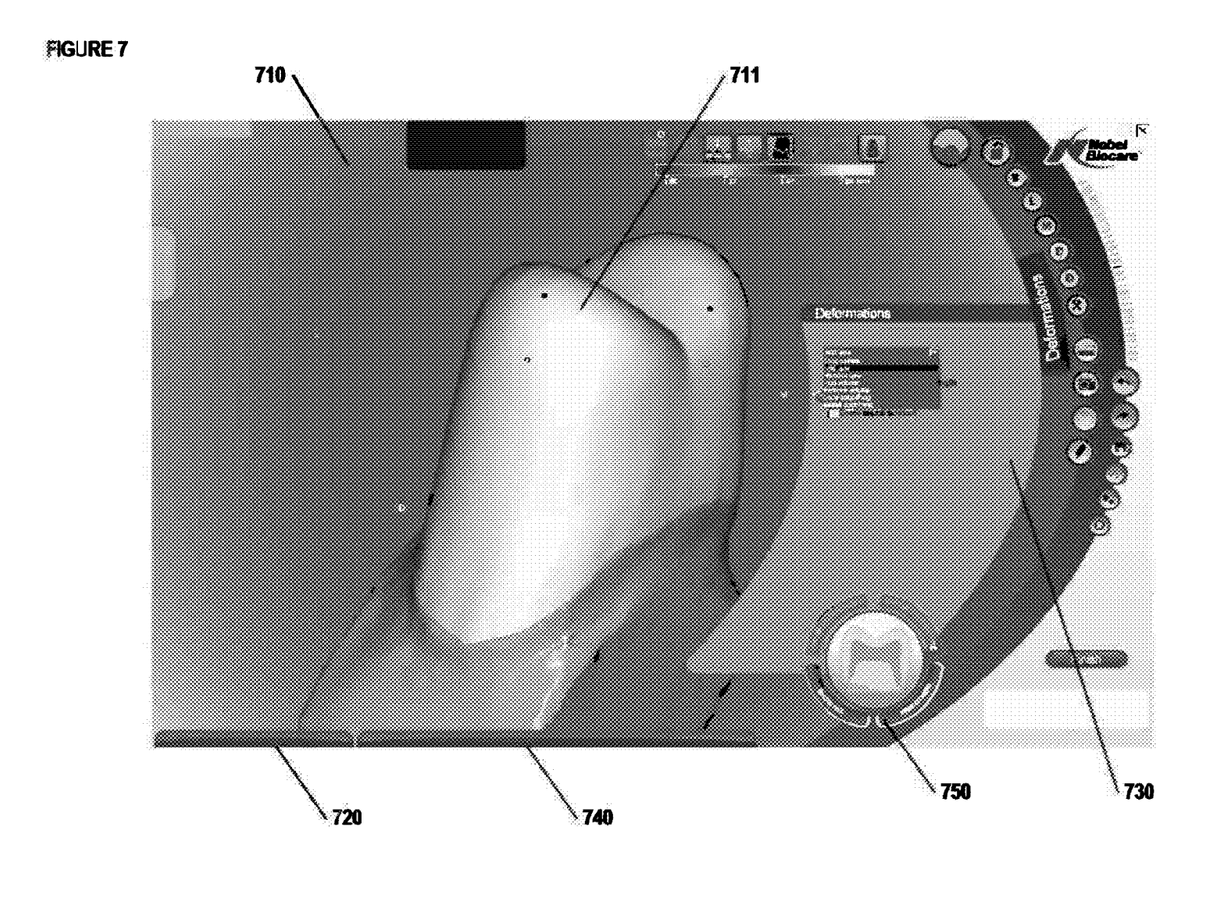
FIG. 7 illustrates a fifth interface for surface manipulation in dental prosthesis design.

FIG. 7 illustrates an interface 700 for surface manipulation in dental prosthesis design. FIG. 7 illustrates that the interface 700 for dental prosthesis design may include more windows than described in some of the previous interfaces. For example, interface 700 may include an overlaid representation portion 710 displaying the surface 711 of the dental prosthesis. The interface may also include a tab for cross-section portion 720, a tab for a localized abstraction portion 740, a globalized abstraction portion 750, and/or a manipulation menu portion 730.

Numerous examples of other interfaces and options for additions of portions of an interface are described in U.S. patent application Ser. No. 12/703,601, filed Feb. 10, 2010, entitled Dental Prosthetics Manipulation, Selection, and Planning, which is hereby incorporated by reference in its entirety for all purposes.

Surface Manipulations in Dental Prosthesis Design

Figure 9:
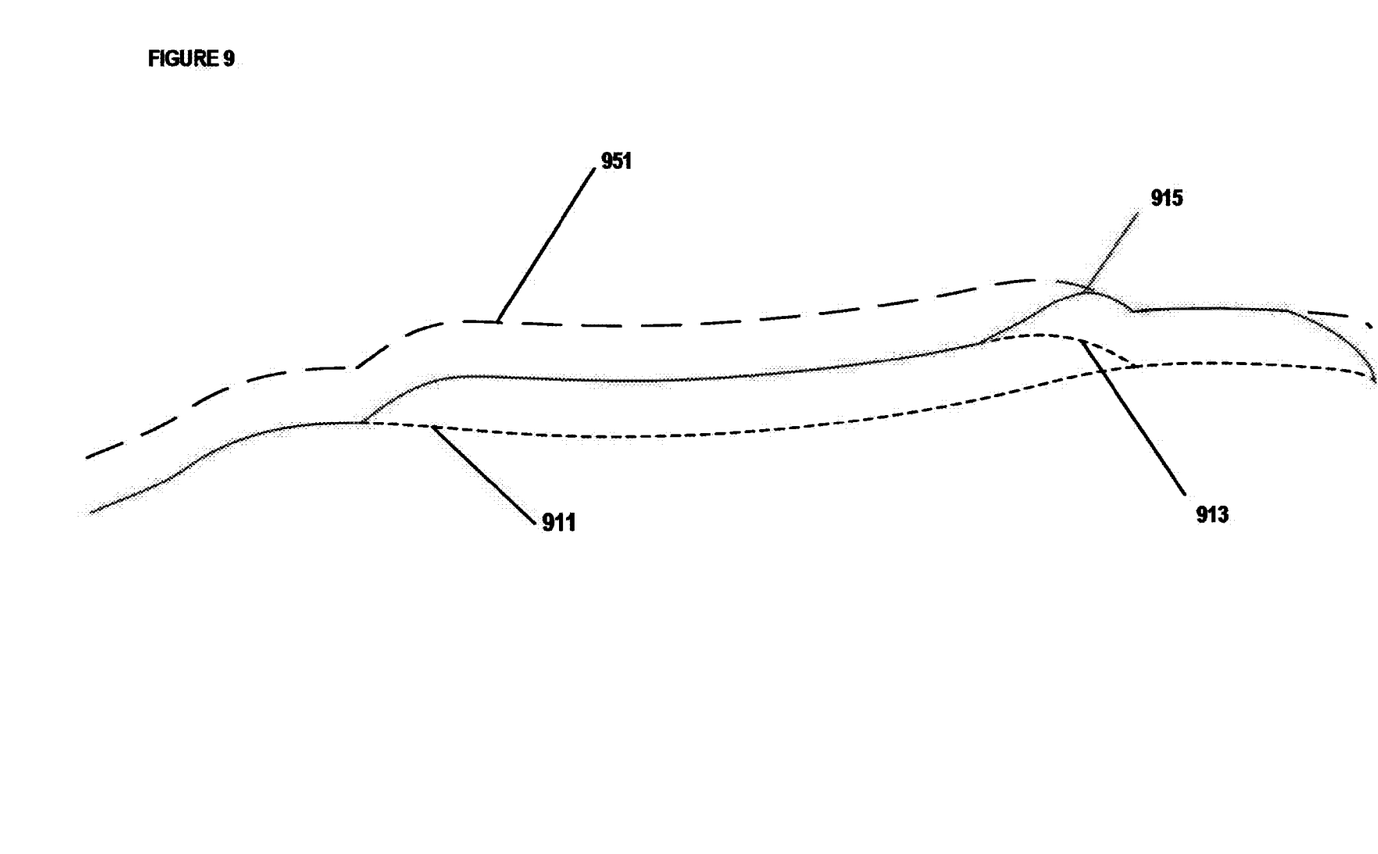
FIG. 9 illustrates a second surface manipulation in dental prosthesis design.
Figure 10:
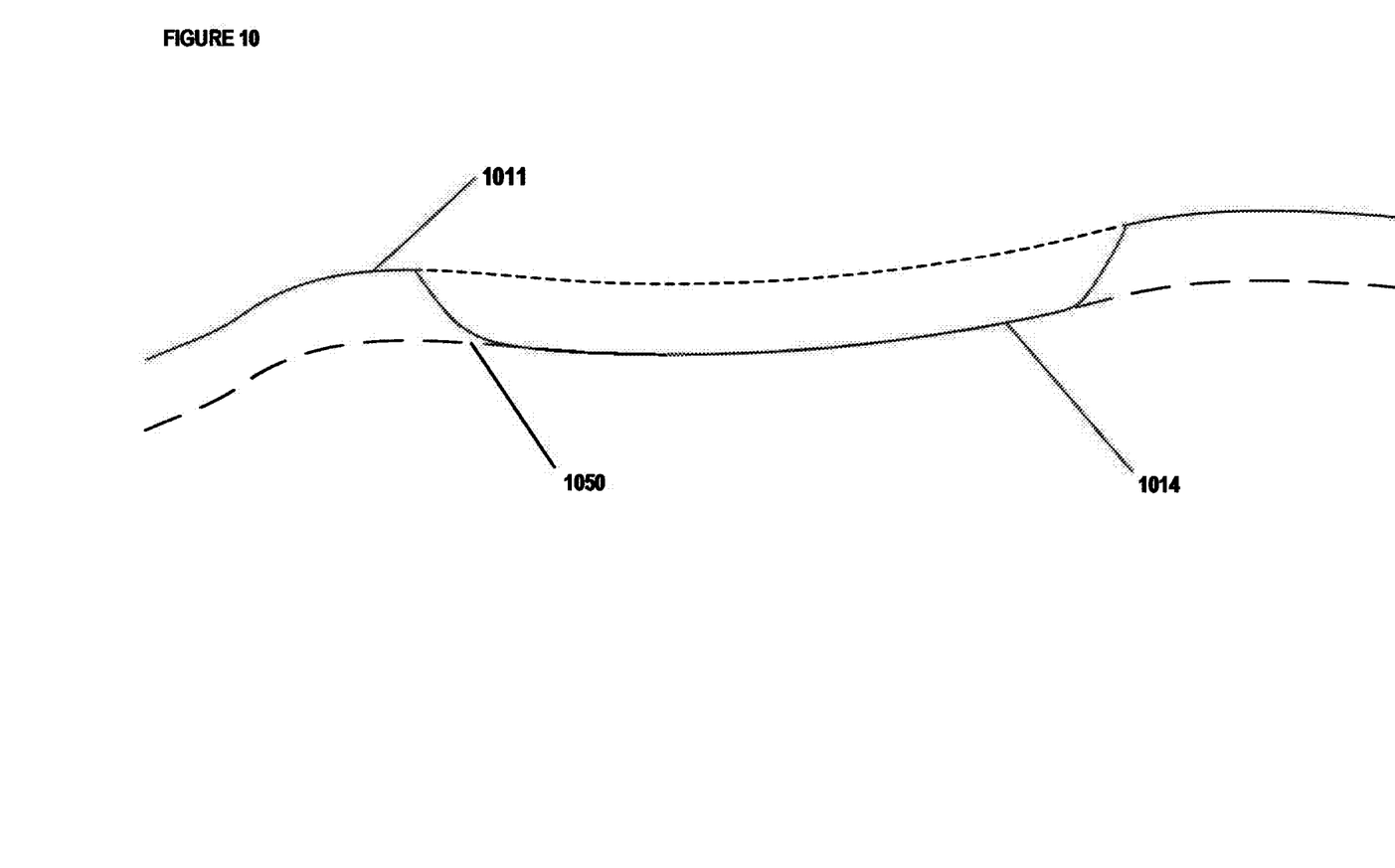
FIG. 10 illustrates a third surface manipulation in dental prosthesis design.

FIGS. 8-10 illustrate examples of manipulating surfaces of dental prostheses. Various examples and embodiments with respect to FIG. 8 have been described elsewhere herein. FIG. 9 shows the second manipulation of a surface 915 being made after a previously manipulated surface 913 has been added to an original surface 911. As illustrated in FIG. 9, after the previously manipulated surface 913 has been added and the manipulation session associated with that manipulation has been completed, that previously manipulated surface 913 is now considered part of the surface, and the new manipulation limit 951 is extended above that previously manipulated surface 913. Therefore, the new manipulation surface 951 tracks accordingly with the previously manipulated surface 913, and not with the original surface 911. When a new manipulation is started, a second manipulation of the surface 915 can be added, and that second manipulation of the surface 915 will add to the surface in the manner described elsewhere herein, up to the new manipulation limit 951.

FIG. 10 illustrates subtraction from, dissection of, or indention into a surface 1011. An original surface 1011 may have portions of that surface indented, taken away, or otherwise manipulated. As with addition to a surface, subtraction from a surface is also associated with a manipulation limit 1050. The operator can provide, using various techniques and embodiments herein, an area to manipulate the surface 1014. Thereafter, the original surface 1011 has the surface subtracted, and the result is a new surface. Subtractions from a surface, such as that depicted in FIG. 10, may be used in conjunction with other subtractions from a surface or other additions to a surface, allowing an operator to variously add and subtract from portions of the surface in order to achieve a desired result.

Other Embodiments

Figure 11:
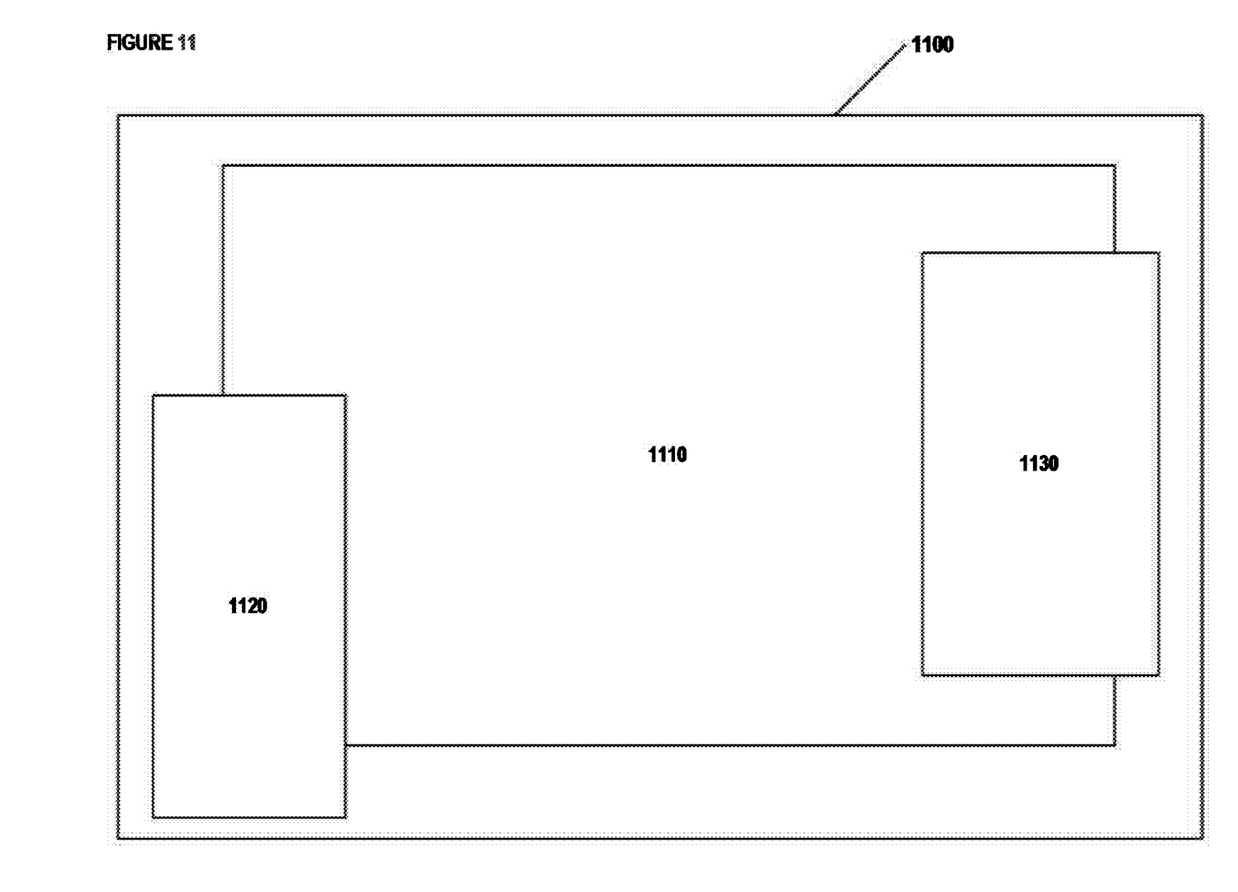
FIG. 11 illustrates a sixth interface for surface manipulation in dental prosthesis design.
Figure 12:
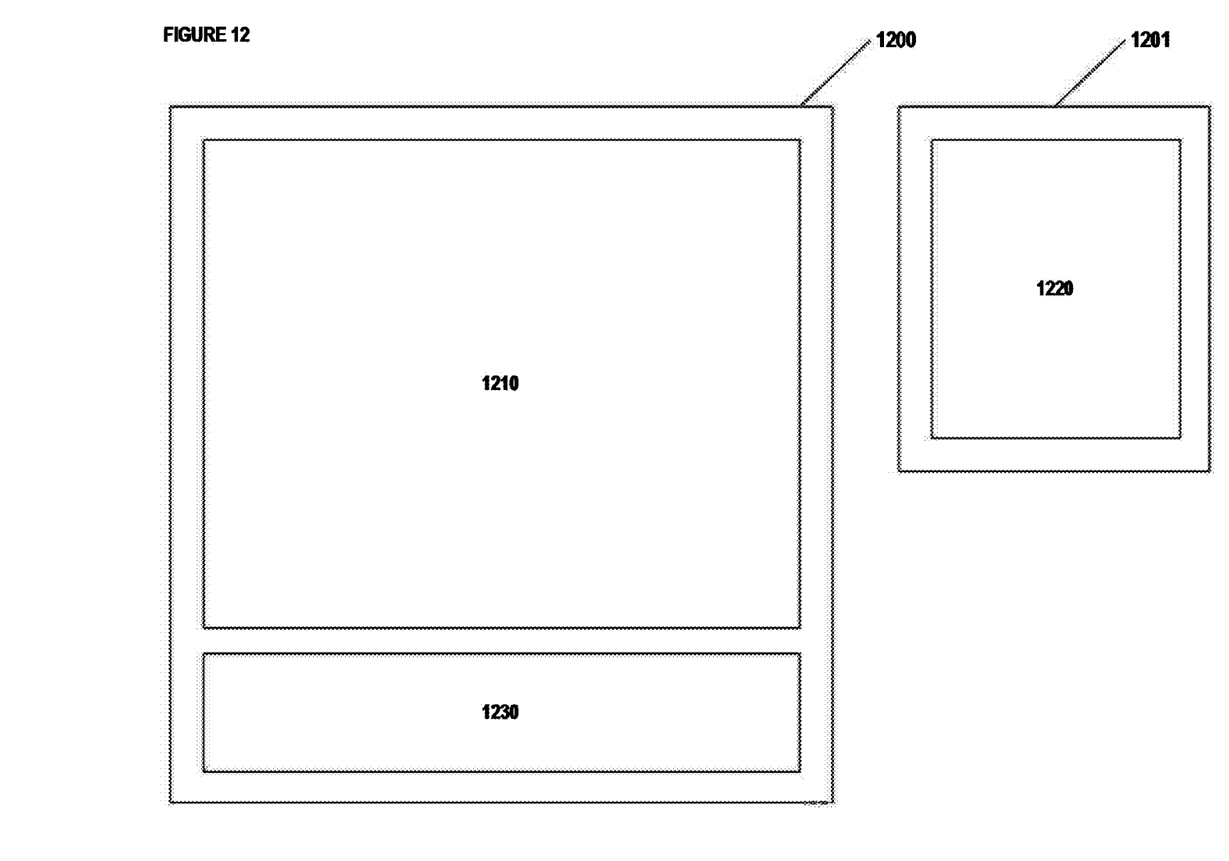
FIG. 12 illustrates a seventh interface for surface manipulation in dental prosthesis design.

FIGS. 11 and 12 illustrate example interfaces for surface manipulation in dental prosthesis design. FIG. 11 illustrates a single interface 1100 that includes a cross-section portion 1120, an overlaid representation portion 1110, and a manipulation menu portion 1130. As illustrated in FIG. 12, the portions of an interface may be displayed on multiple displays, in multiple windows, and/or as part of separate interfaces. FIG. 12 illustrates that an interface may be split into two interfaces 1200 and 1201, with some of the portions being displayed on 1200 and some of the portions being displayed on 1201. For example, interface 1200 may include the overlaid representation portion 1210 and the manipulation portion 1230, while the interface 1201 may include the cross-sectional portion 1220. The interfaces may be displayed on multiple monitors or on a single monitor using a single computer or multiple computers.

The processes and systems described herein may be performed on or encompass various types of hardware, such as computer systems. In some embodiments, computer 210, display 220, and/or input device 230 may each be separate computer systems, applications, or processes or may run as part of the same computer systems, applications, or processes—or one of more may be combined to run as part of one application or process—and/or each or one or more may be part of or run on a computer system. A computer system may include a bus or other communication mechanism for communicating information, and a processor coupled with the bus for processing information. The computer systems may have a main memory, such as a random access memory or other dynamic storage device, coupled to the bus. The main memory may be used to store instructions and temporary variables. The computer systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys.

Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A computer-implemented method for surface manipulation in dental prosthesis design, comprising:
    providing a computer-based interface for modifying a surface of a model of a dental prosthesis;
    receiving via the computer-based interface a set of areas where an operator would like to perform a limited manipulation of the surface of the model, wherein a uniform layer of a thickness is to be added or subtracted in said set of areas, wherein receiving the set of areas comprises receiving a first area in the set of areas and a second area in the set of areas, wherein the first area and the second area overlap in a particular, overlapping area, wherein the first area is not completely within the second area and the second area is not completely within the first area; and
    manipulating portions of the surface up to a predetermined limit associated with the limited manipulation of the surface based on the set of areas, wherein manipulating portions of the surface comprises manipulating a portion of the surface associated with the particular, overlapping area only up to the predetermined limit associated with the limited manipulation, wherein manipulating portions comprises adding or subtracting the uniform layer of the thickness to the first area excluding the overlapping area, the second area excluding the overlapping area, and the overlapping area up to the predetermined limit, wherein manipulating portions of the surface comprises manipulating portions of the surface using one or more computer processors.

2. The method of claim 1, wherein a border band is associated with the edges of the areas in the set of areas and wherein manipulating portions of the surface comprises manipulating portions of the surface less than the limit associated with the limited manipulation at the border band.

3. The method of claim 2, wherein manipulating portions of the surface comprises tapering the manipulation of the border band to zero at the edge of the border band that is away from an associated area in the set of areas.

4. The method of claim 1, wherein manipulating the portions of the surface comprises:
   determining a first manipulation amount based on the first area in the set of areas; and
   determining a second manipulation amount based on the second area in the set of areas.

5. The method of claim 4, wherein manipulating the portions of the surface comprises manipulating a particular portion of the surface by an amount determined based on a maximum of the first manipulation amount and the second manipulation amount.

6. The method of claim 4, wherein manipulating the portions of the surface comprises manipulating a particular portion of the surface by an amount determined based on a function of the first manipulation amount and the second manipulation amount.

7. The method of claim 1, wherein receiving the set of areas comprises receiving areas on the surface of the model.

8. The method of claim 1, wherein receiving the set of areas comprises receiving mouse movements made by the operator.

9. The method of claim 1, wherein receiving the set of areas comprises receiving one or more keystroke.

10. The method of claim 1, wherein the method further comprises receiving a limit associated with a limited manipulation on the surface from the operator.

11. The method of claim 1, wherein receiving the set of areas comprises receiving a set of locations and associating an area with each location.

12. The method of claim 11, wherein the method further comprises receiving a size of areas to associate with each location in the set of locations.

13. A system for surface manipulation in dental prosthesis design, comprising:
   one or more computer processors configured to:
   provide a computer-based interface for modifying a surface of a model of a dental prosthesis;
   receive via the computer-based interface a set of areas where an operator would like to perform a limited manipulation of the surface of the model, wherein a uniform layer of a thickness is to be added or subtracted in said set of areas, wherein the set of areas comprises a first area in the set of areas and a second area in the set of areas, wherein the first area and the second area overlap in a particular, overlapping area, wherein the first area is not completely within the second area and the second area is not completely within the first area; and
   manipulate portions of the surface up to a predetermined limit associated with the limited manipulation of the surface based on the set of areas, wherein the one or more computer processors are configured to manipulate a portion associated with the particular, overlapping area only up to the predetermined limit associated with the limited manipulation, wherein the one or more computer processors are configured to add or subtract the uniform layer of the thickness to the first area excluding the overlapping area, the second area excluding the overlapping area, and the overlapping area up to the predetermined limit.

14. The system of claim 13, wherein a border band is associated with the edges of the areas in the set of areas and wherein the one or more computer processors are configured to manipulate portions of the surface less than the limit associated with the limited manipulation at the border band.

15. The system of claim 13, wherein the one or more computer processors are configured to receive areas on the surface of the model.

16. A non-transitory computer-readable storage medium having embodied thereon in a non-transitory manner computer-executable instructions for performing a method of surface manipulation in dental prosthesis design, the method comprising:
   providing a computer-based interface for modifying a surface of a model of a dental prosthesis;
   receiving via the computer-based interface a set of areas where an operator would like to perform a limited manipulation of the surface of the model, wherein a uniform layer of a thickness is to be added or subtracted in said set of areas, wherein receiving the set of areas comprises receiving a first area in the set of areas and a second area in the set of areas, wherein the first area and the second area overlap in a particular, overlapping area, wherein the first area is not completely within the second area and the second area is not completely within the first area; and
   manipulating portions of the surface up to a predetermined limit associated with the limited manipulation of the surface based on the set of areas, wherein manipulating portions of the surface comprises manipulating a portion of the surface associated with the particular, overlapping area only up to the predetermined limit associated with the limited manipulation, wherein manipulating portions comprises adding or subtracting the uniform layer of the thickness to the first area excluding the overlapping area, the second area excluding the overlapping area, and the overlapping area up to the predetermined limit.

17. The computer-readable storage medium of claim 16, wherein a border band is associated with the edges of the areas in the set of areas and wherein manipulating portions of the surface comprises manipulating portions of the surface less than the limit associated with the limited manipulation at the border band.

18. The computer-readable storage medium of claim 16, wherein receiving the set of areas comprises receiving areas on the surface of the model.

* * * * *